(12) United States Patent
Herth et al.

(10) Patent No.: US 7,973,095 B2
(45) Date of Patent: Jul. 5, 2011

(54) WATER-SOLUBLE OR WATER-SWELLABLE POLYMERS, PARTICULARLY WATER-SOLUBLE OR WATER-SWELLABLE COPOLYMERS MADE OF ACRYLAMIDE AND AT LEAST ONE IONIC COMONOMER HAVING A LOW RESIDUAL MONOMER CONCENTRATION

(75) Inventors: Gregor Herth, Trostberg (DE); Manfred Dannehl, Kahl (DE); Norbert Steiner, Alzenau (DE)

(73) Assignee: Evonik Stockhausen GmbH, Krefeld (DE)

( * ) Notice: Subject to any disclaimer, the term of this patent is extended or adjusted under 35 U.S.C. 154(b) by 104 days.

(21) Appl. No.: 11/814,633

(22) PCT Filed: Jan. 16, 2006

(86) PCT No.: PCT/EP2006/000328
§ 371 (c)(1),
(2), (4) Date: Apr. 16, 2008

(87) PCT Pub. No.: WO2006/079462
PCT Pub. Date: Aug. 3, 2006

(65) Prior Publication Data
US 2008/0200583 A1    Aug. 21, 2008

(30) Foreign Application Priority Data

Jan. 28, 2005  (DE) .................. 10 2005 004 285

(51) Int. Cl.
*C08F 2/48* (2006.01)
*C08F 2/04* (2006.01)
*C08F 2/16* (2006.01)
*C08F 220/56* (2006.01)

(52) U.S. Cl. .............. 522/4; 522/84; 522/175; 522/182; 524/815; 524/827; 524/832

(58) Field of Classification Search ............... 522/84, 522/182, 175, 4, 62, 65; 524/815, 827, 832
See application file for complete search history.

(56) References Cited

U.S. PATENT DOCUMENTS

| | | | | |
|---|---|---|---|---|
| 4,192,727 A * | 3/1980 | Ward | ............ | 521/50.5 |
| 4,376,021 A * | 3/1983 | Okamoto et al. | ........... | 522/4 |
| 4,762,862 A * | 8/1988 | Yada et al. | ........... | 522/3 |
| 5,185,385 A * | 2/1993 | Kanluen et al. | ........... | 522/84 |
| 5,736,497 A | 4/1998 | Steiner | | |
| 6,262,141 B1 * | 7/2001 | Cywar et al. | ........... | 522/42 |
| 6,652,986 B2 | 11/2003 | Peldszus et al. | | |
| 6,818,677 B1 * | 11/2004 | Ito et al. | ........... | 522/28 |
| 6,955,766 B2 | 10/2005 | Schneider et al. | | |
| 2004/0077744 A1 | 4/2004 | Naylor et al. | | |

FOREIGN PATENT DOCUMENTS
JP    63 295604    12/1988

OTHER PUBLICATIONS

U.S. Appl. No. 10/110,545, filed Jul. 8, 2002, Schneider, et al.

* cited by examiner

*Primary Examiner* — Susan W Berman
(74) *Attorney, Agent, or Firm* — Oblon, Spivak, McClelland, Maier & Neustadt, L.L.P.

(57) ABSTRACT

The invention relates to a process for the production of water-soluble or water-swellable polymers having a low content of residual monomers, particularly on the basis of acrylic acid and/or acrylamide and at least one additional water-soluble comonomer, in which process a monomer solution in a polymerizing state is treated with electromagnetic radiation at the earliest after reaching the maximum temperature of polymerization, and the gel obtained is subsequently crushed and dried, and it also relates to the water-soluble or water-swellable polymers as such, which can be obtained according to said process, to their use in the hygiene industry, packaging industry, in the agrarian technology or in agriculture and horticulture, in the cable industry and information technology, in the food industry, papermaking industry, and to their use as flocculation aids and as drilling fluid in petroleum production.

21 Claims, 1 Drawing Sheet

WATER-SOLUBLE OR WATER-SWELLABLE POLYMERS, PARTICULARLY WATER-SOLUBLE OR WATER-SWELLABLE COPOLYMERS MADE OF ACRYLAMIDE AND AT LEAST ONE IONIC COMONOMER HAVING A LOW RESIDUAL MONOMER CONCENTRATION

BACKGROUND OF THE INVENTION

1. Field of the Invention

The invention relates to a process for the production of water-soluble or water-swellable polymers having a low content of residual monomers, particularly on the basis of acrylic acid and/or acrylamide and at least one additional water-soluble comonomer.

2. Description of the Background

Today, water-soluble or water-swellable copolymers are being used industrially in a variety of sectors. For example, they are used in a water-soluble form as flocculation aids in the clarification of municipal and industrial waste waters, as drilling fluids in petroleum production, as soil conditioners, thickening agents, dispersing aids, retention aids, etc.

Also, the fields of use of the corresponding crosslinked water-swellable polymers are highly diverse. Thus, for example, they are used in the personal care industry in the production of hygiene articles such as absorbent sanitary articles for infant and adult hygiene in the form of baby diapers, sanitary towels, tampons, incontinence articles, as well as products for wound dressing, in which they are incorporated.

These products utilize the characteristic absorbing properties of the water-swellable polymers because they are capable of absorbing a multiple of their weight of aqueous liquids or body fluids such as blood or urine with swelling and formation of hydrogels, and of retaining this volume of liquid even upon exposure to external pressure. These properties are utilized in the packaging industry in such a way that nonwoven products having the water-swellable polymers incorporated therein are used as packaging components, particularly in the form of absorbent inserts for fish and meat trays.

Other fields of use of such water-swellable polymers, usually being produced from an aqueous solution, forming a solid gel during polymerization, which is processed into a granular final product in the course of work-up, are agriculture and horticulture where, inter alia, water-swellable polymers are used as soil conditioners for water and nutrient storage, as artificial soil in plant breeding, and as root-protecting gels. In the cable industry and/or information technology, such water-swellable polymers are used as liquid-absorbing and/or liquid-sealing components in electric or optical fiber cables.

More specifically, the increasing use of acrylic acid-based crosslinked water-swellable polymers as so-called superabsorbers in hygiene products has resulted in intense activities of research and development, which are reflected by the range of related patent literature and also represent a direct consequence of the increased demands on the pattern of properties of these polymers made by the personal care industry.

While liquid-absorbing water-swellable polymers with very high swelling power or free swelling capacity upon contact with liquid initially had been used in diaper manufacture with preference, mechanical load studies on diapers led to the discovery that the strain caused by movements of a person wearing the diaper would require a different pattern of properties of the absorbing polymers used in the manufacture of diapers. To ensure liquid absorption, liquid transport, dryness of diaper and skin when using such superabsorbers in diaper constructions, a well-balanced relationship between the absorption capacity of the polymers (gel volume) and the gel strength of the hydrogel forming upon liquid absorption is required in association with high absorption capacity under pressure load.

To obtain superabsorbing polymers with the desired pattern of properties of high retention capacity, high gel strength and high absorption capacity under pressure, the surfaces of the absorbing polymers must be subjected to a subsequent treatment. Subsequent surface treatment has often been described in the patent literature:

Thus, U.S. Pat. No. 4,043,952 recommends polyvalent metal compounds to improve the dispersibility in water, and U.S. Pat. No. 4,051,086 recommends glyoxal to improve the absorption rate.

DE-OS 27 40 169 describes the production of absorbents based on polymers containing potassium acrylate and ammonium acrylate, which have been treated with polyols and used as powders and films in diapers and other hygiene products and in medical articles.

The patent documents EP 0 083 022, DE-OS 33 31 644, DE-OS 35 07 755, DE-OS 35 23 617, DE-OS 36 28 482, and EP 0 349 240 describe subsequent treatment of resins with crosslinking agents including two or more functional groups which may undergo reaction with the carboxyl or carboxylate groups or other groups contained in the polymer. Here, the powder is either mixed directly with the components, optionally co-using minor amounts of water and solvent, or the powder is dispersed in an inert solvent, or polymers containing 10 to 40 wt.-% water are dispersed in a hydrophilic or hydrophobic solvent and subsequently or simultaneously mixed with the crosslinking agent. Polyglycidyl ethers, haloepoxy compounds, polyols, polyamines or polyisocyanates can be used as crosslinking agents.

In addition to the above, DE-OS 33 14 019, DE-OS 37 37 196 also mention polyfunctional aziridine compounds, alkyl di(tri)halides and oil-soluble polyepoxy compounds.

In DE-OS 35 03 458, a crosslinking agent is applied on a polymer in the presence of an inert inorganic powder such as $SiO_2$, without using organic solvents.

According to DE 40 20 780 C1, improved absorption under pressure is achieved by surface-crosslinking treatment of a polymer resin with 0.1 to 5 wt.-% of an alkylene carbonate.

All of the above-mentioned methods have in common that applying the surface-crosslinking agent is followed by thermal treatment of the polymers.

In view of the primary use of such crosslinked absorber polymers in the hygiene sector, special care should be taken that the polymers intended for use in baby diapers or other hygiene articles would not cause any skin-sensitizing effects in the user of such products. More specifically, it must be ensured that the starting materials and crosslinking agents used in the production process are reacted in such a way that any potential of hazard to health of the final product can be excluded, because the final product is to be rated as safe in toxicological terms, i.e., the polymers must have zero or only a very low content of residual monomers whose toxicity has been well researched by experiments.

However, this not only applies to polymers intended for use in hygiene products, but also to water-soluble and water-swellable polymers based on acrylamide. Thus, the toxic potential of acrylamide has been known for a long time, and a large number of patents and publications are dealing with the reduction of acrylamide in such polymer products. One way of achieving a reduction of the residual monomer content of acrylamide is based on the addition of an additive following polymerization, which adds to the double bond of the acrylamide residual monomer, thereby reacting same.

It has been found, however, that complete conversion of the monomers, especially monomers based on acrylic acid and those based on acrylamide, is not possible in the production of water-soluble or water-swellable polymers. Thus, it has been determined that the production of a crosslinked water-swellable polymer having the desired properties of high absorption rate, high retention capacity and high absorption under pressure load, in association with a residual monomer content as low as possible, depends—among other things—on the crosslinker concentration and the polymerization catalysts being used.

High retention capacity is achieved in a polymer having a low level of crosslinking. In contrast, high absorption under pressure requires a highly crosslinked and thus stabilized polymer which is capable of swelling against external pressure only as a result of its stability. As crosslinking increases, however, the residual monomer content likewise increases, because the rapidly increasing viscosity during production of the polymer reduces diffusion of the residual monomer molecules to the reactive free-radical centers. Moreover, catalyst systems reducing the level of residual monomers or high-level catalyst systems frequently result in an undesirable reduction of retention.

Due to the above-mentioned problems in conducting a polymerization process in such a way that virtually no residual monomers would be formed, and as a result of the toxicological safety demanded of the final product, various methods have been proposed in which the residual monomers are removed from the previously produced polymers by converting the former into harmless derivatives.

For example, DE-AS 10 70 377 and U.S. Pat. No. 2,960,486 describe treatment of the high-molecular weight polymer gel, which is obtained following polymerization, with aqueous sodium disulfite or sodium metabisulfite solution and drying thereof at 80 to 120° C., thus obtaining a residual acrylamide content of 0.01%. Due to their economic inefficiency, these methods failed to achieve general acceptance in practice, because they require processing of the polymer products in a highly diluted (2 to 3%) polymer solution.

Likewise, JP-PS 56/103207 uses bisulfites, sulfites and pyrosulfites to reduce the level of residual monomers. U.S. Pat. No. 3,780,006 uses gaseous sulfur dioxide in order to decrease the acrylamide concentration in an emulsion polymer.

The treatment of a polymer gel with an aqueous solution of sodium bisulfite or metabisulfite has been described in U.S. Pat. No. 3,755,280, and with a solid alkali sulfite in EP 175,554, where residual monomer contents of from 0.03 to 0.3 wt.-% have been obtained.

EP 0 505 163 describes a secondary treatment of crosslinked acrylic acid polymers with a combination of metabisulfite and a surface-active substance (HLB from 3 to 40), thereby decreasing the residual monomer content down to 10 ppm. From 2 to 5 wt.-% of metabisulfite (relative to the polymer gel having 40% w.s., that is, from 5 to 12.5 wt.-% of metabisulfite relative to the dry polymer product) is necessary in such a secondary treatment of polymers in order to achieve the above-mentioned decrease in residual monomers. Such high quantities of added substances may have adverse effects on the technological properties.

WO 94/20547 describes additives such as bromates and chlorates in the polymerization solution and subsequent heating of the final polymer wherein, inter alia, a decrease of the residual monomers is effected by the additives. The bromates and chlorates may also be added subsequent to the polymerization. Despite these measures, the residual monomer content of the polymer products is between about 135 and 1100 ppm.

EP 0 303 518 A2 describes a continuous and discontinuous process, respectively, for the production of crosslinked polyacrylate resins, wherein acrylic acid with a degree of neutralization of 70 to 100 mole-% and a water-miscible or water-soluble polyvinyl monomer are polymerized in aqueous solution. The aqueous monomer solution to be polymerized has a monomer concentration of at least 50%, and a combination of a thermal polymerization initiator and a redox initiator is employed to reduce the level of monomers. The polymerization is conducted in such a way that the exothermic heat of reaction generated during polymerization is essentially the only thermal energy that is used to perform polymerization, crosslinking and evaporation of the water employed, so that subsequent drying can be omitted. In general, the polymer products obtained in this way are said to have residual monomer contents below 500 ppm, preferably below 200 ppm.

While the above-mentioned processes allow production of polymers with reduced residual monomer content, they frequently require complicated reaction engineering, considerably raising the production cost of the polymer products. In particular, secondary treatment with sulfur-containing compounds, part of which remain in the final product as additives, must be regarded as disadvantageous. Such secondary treatment—as an additional reaction step—not only involves the use of additional apparatus or equipment etc., i.e., is associated with an additional input of time and, as a consequence, cost, but also, it does not exclude formation of oxidation products of sulfur which must be taken into account not only from an environmental point of view, but also, in particular, technologically with respect to corrosion resistance of the plant.

Furthermore, treatment with cysteine is not possible for water-soluble copolymers, because this would give rise to crosslinking and, as a consequence, insolubility of the product. Moreover, the high amounts of sulfite, in some cases 2 to 3% relative to the weight of the product, have an extremely negative effect on the technological properties of the product.

DE 35 39 385 therefore claims treatment of acrylamide polymers and copolymers with amines.

DE 19 752 127 and DE 19 752 128 describe addition of ammonia and amines or ammonium salts to the monomer solution. This process is disadvantageous in that the product must be dried above 120° C. in order to obtain the desired effect. This results in a significantly deteriorated solubility for water-soluble polymers as a result of crosslinking reactions taking place at elevated temperature. In particular, this applies to copolymers including non-ionic comonomers such as sodium acrylate in addition to acrylamide.

WO 01/25289 describes irradiation of the polymer gel following crushing. Therein, polymerization is effected in the absence of light and in the presence of a UV initiator which is activated by UV light following crushing. The same procedure has been described in WO 01/55228.

These methods involve the following drawbacks:
a) An additional additive (photoinitiator) not utilized in the actual polymerization must be added to the monomer solution.
b) The actual polymerization must be carried out in the absence of light, which is complicated in terms of production technology.
c) Due to its short wavelength, UV light has only a short penetration depth into the polymer following crushing.

The object of the present invention was to devise a process that would furnish polymers, especially on the basis of acrylic acid or acrylamide, which contain a very low or zero residual content of residual monomers, in which process the amount of unreacted monomers is to be significantly reduced or brought to complete conversion even during polymerization, so that operation may proceed using less residual monomer scavenger or none at all. Furthermore, the process should work without additives having no function during polymerization, or, in other words, it should be possible to perform the process in a continuous fashion on a continuous belt.

SUMMARY OF THE INVENTION

Surprisingly, it was found that said object is accomplished by means of a process for the production of polymers, wherein a monomer solution in a state of polymerization is treated with electromagnetic radiation at the earliest after reaching the maximum temperature of polymerization, $T_{max}$, and the gel obtained is subsequently crushed and dried.

DETAILED DESCRIPTION OF THE INVENTION

Preferably, the monomer solution is polymerized to a monomer conversion of 95 percent and, particularly preferred according to the invention, to a monomer conversion of 99 percent, before treatment with electromagnetic radiation is effected.

The monomer solution, which is used according to the invention in order to produce the polymer products, comprises anionic, non-ionic, as well as cationic and amphiphilic ethylenically unsaturated monomers.

According to the invention, the following monomers illustrated as examples below can be used or selected as anionic monomers:

a) olefinically unsaturated carboxylic acids, carboxylic anhydrides and carboxylic nitriles, particularly acrylic acid, methacrylic acid, itaconic acid, crotonic acid, glutaconic acid, maleic acid, maleic anhydride, fumaric acid, and water-soluble esters and/or alkali, alkaline earth metal and ammonium salts thereof;

b) olefinically unsaturated sulfonic acids, particularly aliphatic and/or aromatic vinylsulfonic acids, e.g. vinylsulfonic acid, allylsulfonic acid, styrenesulfonic acid, acryl- and methacrylsulfonic acids, particularly sulfoethyl acrylate, sulfoethyl methacrylate, sulfopropyl acrylate, sulfopropyl methacrylate, 2-hydroxy-3-methacryloxypropylsulfonic acid and 2-acrylamido-2-methylpropanesulfonic acid, and water-soluble alkali, alkaline earth metal and ammonium salts thereof;

c) olefinically unsaturated phosphonic acids, particularly e.g. vinyl- and allyl-phosphonic acid and water-soluble alkali, alkaline earth metal and ammonium salts thereof;

d) sulfomethylated and/or phosphonomethylated acrylamides and water-soluble alkali, alkaline earth metal and ammonium salts thereof.

In a preferred fashion, olefinically unsaturated carboxylic acids and carboxylic anhydrides, particularly acrylic acid, methacrylic acid, itaconic acid, crotonic acid, glutaconic acid, maleic acid, maleic anhydride, fumaric acid and water-soluble esters and/or alkali, alkaline earth metal and ammonium salts thereof are employed as anionic monomers, and the water-soluble alkali salts of acrylic acid, especially the sodium and potassium salts, as well as the ammonium salts, are particularly preferred.

For example, non-ionic monomers used in the production of the polymers A are compounds of general formula (I)

(I)

wherein
$R^1$ represents hydrogen or a methyl residue, and
$R^2$ and $R^3$ independently represent hydrogen, an alkyl or hydroxyalkyl residue with 1 to 5 C atoms and an OH group.

In a preferred fashion, (meth)acrylamide, N-methyl(meth)acrylamide, N-isopropyl(meth)acrylamide or N,N-substituted(meth)acrylamides such as N,N-dimethyl(meth)acrylamide, N, N-diethyl(meth)acrylamide, N-methyl-N-ethyl(meth)acrylamide or N-hydroxyethyl(meth)acrylamide are used.

According to the invention, especially the water-soluble or water-dispersible derivatives of acrylic and methacrylic acid, such as acrylamide, methacrylamide and n-alkyl-substituted acrylamides, can be used with advantage as non-ionic monomers, and, according to the invention, acrylamide is particularly preferred as non-ionic monomer.

In addition to the non-ionic monomers specified above, other monomers such as acrylonitrile, vinylpyridine, vinyl acetate, hydroxy group-containing esters of polymerizable acids, as well as hydroxyalkyl, especially hydroxyethyl and -propyl esters of acrylic acid and methacrylic acid, can be used according to the invention.

Suitable as likewise usable cationic monomers for the production of the polymer products according to the invention are compounds of general formula (II)

wherein
$R_1$ represents hydrogen or a methyl residue,
$Z_1$ represents O, NH or $NR_4$, with $R_4$ representing an alkyl residue with 1 to 4 C atoms,
Y represents one of the groups wherein
$Y_0$ and $Y_1$ represent an alkylene residue or hydroxyalkylene residue with 2 to 6 C atoms,
$Y_2, Y_3, Y_4, Y_5, Y_6, Y_7$ independently represent an alkyl residue with 1 to 6 C atoms,
$Z^-$ represents halogen, acetate, $SO_4CH_3^-$.

In a preferred fashion, protonated or quaternized dialkylaminoalkyl(meth)acrylates or (meth)acrylamides with 1 to 3

C atoms in the alkyl or alkylene groups are suitable, more preferably the methyl chloride-quaternized ammonium salts of dimethylaminoethyl(meth)acrylate, dimethylaminopropyl(meth)acrylate, dimethylaminoethyl(meth)acrylate, diethylaminoethyl(meth)acrylate, dimethylaminomethyl(meth)acrylate, dimethylaminoethyl(meth)acrylamide and/or dimethylaminopropyl(meth)acrylamide.

Also suitable as amphiphilic monomers are compounds of general formula (III) or (IV)

wherein
$Z_1$ represents O, NH, $NR_4$, with $R_4$ representing alkyl with 1 to 4 carbon atoms,
$R_1$ represents hydrogen or a methyl residue,
$R_4$ represents alkylene with 1 to 6 carbon atoms,
$R_5$ and $R_6$ independently represent an alkyl residue with 1 to 6 carbon atoms,
$R_7$ represents an alkyl, aryl and/or aralkyl residue with 8 to 32 carbon atoms, and
$Z^-$ represents halogen, pseudohalogen, $SO_4CH_3^-$ or acetate, or wherein
$Z_1$ represents O, NH, $NR_4$, with $R_4$ representing alkyl with 1 to 4 carbon atoms,
$R_1$ represents hydrogen or a methyl residue,
$R_8$ represents hydrogen, an alkyl, aryl and/or aralkyl residue with 8 to 32 carbon atoms,
$R_9$ represents an alkylene residue with 2 to 6 carbon atoms, and
n represents an integer of 1 and 50.

In a preferred fashion, reaction products of (meth)acrylic acid and polyethylene glycols (10 to 40 ethylene oxide units), etherified with a fatty alcohol, or the corresponding reaction products with (meth)acrylamide are concerned.

For the production of the polymer products produced according to the process of the invention, a monomer composition comprising 0 to 100 wt.-%, preferably 5 to 70 wt.-%, more preferably 15 to 40 wt.-%, relative to the overall amount of monomers, of preferably anionic monomers, is selected for the polymerizing monomer solution in the event of water-soluble polymers. In a particularly preferred fashion, a mixture of non-ionic monomers, preferably acrylamide, and anionic monomers, especially olefinically unsaturated carboxylic acids and carboxylic anhydrides, preferably acrylic acid, methacrylic acid, itaconic acid, crotonic acid, glutaconic acid, maleic acid, maleic anhydride, fumaric acid, and water-soluble esters and/or alkali, alkaline earth metal and ammonium salts thereof, is used in the production of the water-soluble polymers, with acrylic acid being particularly preferred as anionic monomer.

Also preferred is a mixture of acrylic acid with alkyl(meth)acrylates and/or alkyl(meth)acrylamides.

Water-swellable polymers as water-absorbing absorbents are obtained using at least one crosslinker. As crosslinkers, those compounds are used which contain at least two or more functional groups (double bonds, epoxy groups) and are capable of being incorporated in the growing polymer chains during polymerization.

As a result, crosslinking sites are formed at various positions in the polymer product, which hold together the individual polymer chains, taking such an effect that the polymer particles can merely swell in a liquid and will not dissolve in said liquid. The properties of the crosslinked polymer are determined by the chemical structure of the crosslinker, the number of crosslinking sites, but also, by their distribution in the polymer chains. In case of optimum incorporation of crosslinker in the polymer, crosslinked polymer products will be formed wherein the crosslinking sites are uniformly distributed, so that non-crosslinked regions or even non-crosslinked (i.e., water-soluble) low molecular weight components are barely present in the polymer product. Uniform distribution of the crosslinking sites within the polymer results in a product which also has optimum retention capability for aqueous liquids and optimum gel strength in swelled state.

Primarily, the monomers to be used according to the invention in order to produce the monomer solution for the production of water-swellable polymers are acrylic acid, methacrylic acid, acrylamide and methacrylamide, which, when used alone, are polymerized to form homopolymers or mixed polymers, but also other water-soluble monomers such as acrylonitrile, methacrylonitrile, N,N-dimethylacrylamide, vinylpyridine, vinyl acetate, as well as other water-soluble polymerizable acids and salts thereof, particularly maleic, fumaric, itaconic, vinylsulfonic, or acrylamidomethylpropanesulfonic acids; also, hydroxy group-containing esters of polymerizable acids, particularly hydroxyalkyl esters, preferably hydroxyethyl and hydroxypropyl esters of acrylic and methacrylic acid can be used; furthermore, amino group-containing and ammonium group-containing esters and amides of polymerizable acids, such as dialkylamino esters, particularly the dimethyl- and diethylaminoalkyl esters of acrylic and methacrylic acid, as well as trimethyl- and trimethylammoniumalkyl esters and the corresponding amides. The above monomers can be polymerized alone to form homopolymers or mixed with each other to form mixed polymers.

In addition, small amounts of water-insoluble monomers can be copolymerized with the above monomers, e.g. esters of acrylic and/or methacrylic acid with $C_1$-$C_{10}$ alcohols, styrene and alkylated styrenes. In general, the proportion of water-soluble monomers in the monomer solution is from 60 to 100 wt.-%, particularly 80 to 100 wt.-%, relative to the overall monomers, with acrylic acid being preferred as monomer. As a rule, the water-insoluble (hydrophobic) monomers make up for 0 to 40 wt.-% of the monomers.

The acrylic acid or derivatives thereof required for polymerization are purified by distillation and subsequently neutralized to a level of preferably at least 30 mole-%. Once the desired neutralization ratio is established, the polymerization reaction should be started immediately. The monomers to be employed, especially acrylic acid, should always be freshly purified prior to polymerization, because e.g. prolonged storage of the acrylic acid monomers, in association with high storage temperature, will result in an undesirable increase of the diacrylic acid content in the monomer solution, which may give rise to an increased residual monomer content in the polymer product.

The acid groups in the aqueous monomer solutions are neutralized with bases according to well-known methods, the degree of neutralization preferably being at least 30 mole-%, especially between 50 and 100 mole-%, and more preferably between 70 and 95 mole-%. Possible as bases for neutralization are all common inorganic and organic compounds, which can be used alone or in mixed combinations for neutralization. Apart from sodium and potassium hydroxide solution and the corresponding carbonates, preferred neutralization agents are basic nitrogen compounds, such as ammonia or ammonium hydroxide, ammonium salts, as well as amino compounds such as aliphatic, cycloaliphatic, heterocyclic and aromatic mono- and polyamines, hydroxylamines and alkanolamines. Particularly preferred nitrogen compounds are ammonia or ammonium hydroxide, hydroxylamine, ethanolamine, diethanolamine, as well as mixtures thereof.

To produce water-swellable polymers, minor amounts of crosslinking monomers, e.g. monomers having more than one reactive group in their molecule, can be polymerized together with the above-mentioned monomers. Such crosslinkers, which contain at least two or more functional groups, e.g. double bonds, epoxy groups, are capable of being incorporated in the growing polymer chains during polymerization. As a result, crosslinking sites are formed at various positions in the polymer product, which hold together the individual polymer chains, taking such an effect that the polymer particles can merely swell in a liquid and will not dissolve in said liquid. The properties of the crosslinked polymer are determined by the chemical structure of the crosslinker, the number of crosslinking sites, but also, by their distribution in the polymer chains. In case of optimum incorporation of the crosslinker in the polymer, crosslinked polymer products will be formed wherein the crosslinking sites are uniformly distributed, so that non-crosslinked regions or even non-crosslinked (i.e., water-soluble) low molecular weight components are barely present in the polymer product. Uniform distribution of the crosslinking sites within the polymer results in a product which also has optimum retention capability for aqueous liquids and optimum gel strength in the swelled state.

Multifunctional monomers, e.g. amides such as methylenebisacrylamide or -methacrylamide or ethylenebisacrylamide, and also, esters of polyols, such as diacrylates or triacrylates, e.g. butanediol or ethylene glycol diacrylate, polyglycol di(meth)acrylates, trimethylolpropane triacrylate, di- and triacrylate esters of trimethylolpropane preferably oxyalkylated (ethoxylated) with 1 to 30 moles of alkylene oxide, acrylate and methacrylate esters of glycerol and pentaerythritol, or of glycerol and pentaerythritol preferably oxyethylated with 1 to 30 mol ethylene oxide, and also, allyl compounds such as allyl(meth)acrylate, triallyl cyanurate, diallyl maleate, polyallyl esters, tetraallyloxyethane, triallylamine, tetraallylethylenediamine, allyl esters of phosphoric acid or phosphorous acid, and crosslinkable monomers such as N-methylol compounds of amides such as methacrylamide or acrylamide and ethers derived therefrom may be mentioned as examples of crosslinking monomers. The proportion of crosslinking monomers is from 0 to 10 wt.-%, preferably from 0.01 to 3.0 wt.-%, relative to the overall monomers.

Polymerization of the monomer solution is effected using standard initiators or redox systems inducing free-radical polymerization. In order to achieve an economic production of the polymers, the polymerization is preferably carried out using initiators which decompose at relatively low temperatures.

Conventionally, the polymerization is carried out as an adiabatic polymerization, in which case the reaction can be initiated using a redox system as well as a photoinitiator. A combination of both initiating variants is also possible.

The redox initiator system preferably consists of two components, namely, an organic or inorganic oxidizing agent and an organic or inorganic reducing agent. Frequently, compounds having peroxide units are employed, e.g. inorganic peroxides, especially alkali metal and ammonium persulfates, alkali metal and ammonium perphosphates, hydrogen peroxide and salts thereof, e.g. sodium peroxide and barium peroxide, or organic peroxides such as benzoyl peroxide, butyl hydroperoxide, or peracids such as peracetic acid. In addition, other oxidizing agents can be used, e.g. potassium permanganate, sodium and potassium chlorate, potassium dichromate, etc. As reducing agent, sulfur-containing compounds such as sulfites, thiosulfates, sulfinic acid, organic thiols, especially ethylmercaptane, 2-hydroxyethanethiol, 2-mercaptoethylammonium chloride, thioglycolic acid and others can be used. Also possible is the use of ascorbic acid and low-valent metal salts such as copper(I), manganese(II), iron(II). The use of phosphorus compounds is also possible. Sodium hypophosphite may be mentioned as example.

In the event of a photopolymerization, the reaction is initiated by means of UV light which causes decomposition of the initiator. As initiators, benzoin and benzoin derivatives, such as benzoin ethers, benzil and derivatives thereof, such as benzil ketals, acrylic diazonium salts, azo initiators such as 2,2'-azobisisobutyronitrile, 2,2'-azobis(2-amidinopropane) hydrochloride or acetophenone derivatives can be used. The amounts of the oxidizing and reducing components may range between 0.0005 and 0.5% by weight, preferably from 0.001 to 0.1% by weight, relative to the monomer solution, and the amounts of photoinitiators may range between 0.001 and 0.1% by weight, preferably from 0.002 to 0.05% by weight.

The polymerization is preferably performed in aqueous solution, batchwise in a polymerization vessel or continuously on a continuous belt, e.g. according to DE 35 44 770 which, by reference, is hereby incorporated in the description of the present patent application.

Given a virtually adiabatic course of polymerization, an aqueous polymer gel is formed at an appropriate initial concentration of 15 to 50 wt.-%. By selecting the initial monomer concentration and an appropriate initial temperature ranging from −20 to +50° C., preferably from −10 to +10° C., it is possible to control the temperature profile in such a way that easy control of the reaction is possible.

One essential issue to the process according to the invention is that the monomer solution in polymerizing state be treated with electromagnetic radiation, preferably infrared radiation, at the earliest after reaching the maximum temperature of polymerization, because very high conversion of the monomers can be assumed at this point in time. In a preferred fashion the polymer gel obtained during polymerization is treated with electromagnetic radiation at a monomer conversion of 95% and more preferably at least 99%.

For example, IR radiation, microwave radiation, VIS, but also, UV radiation can be used as electromagnetic radiation in the process according to the invention, particularly in a frequency range $\nu=10^9$ to $10^{16}$ Hz, corresponding to a wavelength range $\lambda=35$ cm to 3 nm, to which end the use of IR radiation is particularly preferred. When using IR radiation, a wavelength range $\lambda=750$ to 25,000 nm is preferred, and when using visible light (VIS radiation), the preferred wavelength range is $\lambda=380$ to 750 nm. When using UV radiation, it is preferred to use it in a wavelength range $\lambda=172$ to 380 nm, corresponding to a frequency range $\nu=900$ MHz to 140 GHz.

Regarding the possible use of UV radiation in the process according to the invention, it should be noted that, in the event of photopolymerizations where the reaction is initiated with UV light, i.e. UV radiation, it is familiar to maintain irradiation with such UV light during the entire polymerization reaction so as to ensure complete decomposition of the photoinitiator. Again, it was a complete surprise to find that treatment according to the invention, in this case additional treatment, with electromagnetic radiation at the earliest after reaching the maximum temperature of polymerization, said electromagnetic radiation having a longer wavelength than the UV light used for the decomposition of the photoinitiator, polymer products are obtained, particularly based on acrylic acid or acrylamide, which contain exceedingly low or zero residual content of residual monomers. An essential issue to the above embodiment of the invention is that the electromagnetic radiation used has a longer wavelength than the UV light used for the decomposition of the photoinitiator. Particularly preferred to this end is IR radiation.

Depending on the type of radiation used, the time period of treatment with electromagnetic radiation in the process according to the invention is 0 to 60 minutes, preferably 3 to 25 minutes, and more preferably 5 to 20 minutes.

After the polymerization is completed, the polymer present in the form of a gel is crushed. Thereafter, the crushed gel is dried discontinuously e.g. in a circulating air oven at 70 to 150° C., preferably at 80 to 130° C. Continuous drying can be effected in the same temperature range using a belt dryer or a fluid-bed dryer.

Following drying, the polymers produced according to the invention are milled to the desired grain fraction and subsequently classified into the screen fractions required for different uses. For example, grain size distributions of from 0.2 to 1 mm are preferred for the use of crosslinked polymer products as absorbents in the hygiene sector. For use in agriculture and horticulture, products having a grain size distributions of from 0.2 to 3 mm are employed, whereas products ranging from 0.1 to 1.2 mm are preferred in soluble polymers for use as flocculants. To achieve rapid dissolution of the product, in particular, at least 90 percent of the product should be below 2.0 mm, and preferably 90 percent below 1.5 mm in size.

In a preferred embodiment of the invention, especially for the production of water-swellable superabsorbing polymers with the desired pattern of properties of high retention capacity, high gel strength and high absorption capacity under pressure, the surfaces of these absorbing polymers are subjected to a subsequent treatment so as to meet the high demands made by the personal care industry on such polymers when used in hygiene products. In such secondary crosslinking, which results in a significant improvement of gel stability, liquid absorption under pressure, and absorption rate, associated with a low content of residual monomers, compounds are preferably used which have at least two functional groups and are capable of crosslinking the functional groups of the polymer product on the surface of the polymer particles.

Crosslinkers having alcohol, amine, aldehyde, glycidyl, epichloro functions, such as polyhydric alcohols, polyepoxy compounds, polyglycidyl compounds, polyamines, polyfunctional aziridine compounds, polyaldehydes, polyisocyanates, polyoxazolines, alkylene carbonates, and polyvalent metal compounds should be mentioned, and it is also possible to use crosslinker molecules having several different functions. The following secondary crosslinking agents may be mentioned as examples: ethylene glycol, diethylene glycol, triethylene glycol, polyethylene glycol, glycerol, polyglycerol, propylene glycol, diethanolamine, triethanolamine, propylene oxide, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, propylene carbonate, and polyepoxides such as ethylene glycol diglycidyl ethers, with ethylene carbonate being particularly preferred.

The above-mentioned crosslinkers can be used alone, but also as mixtures of a plurality of the above-mentioned crosslinkers, both directly and as aqueous alcoholic or aqueous solution, in surface crosslinking of the polymer products. The secondary crosslinkers are employed in amounts of from 0.01 to 10 wt.-%, preferably from 0.1 to 5 wt.-%, and more preferably from 0.1 to 1.0 wt.-%, relative to the polymer to be subjected to secondary crosslinking.

To achieve the desired properties, uniform distribution of the secondary crosslinking agent on the polymer particles is required. Suitable mixing units for applying the secondary crosslinking agent are e.g. Patterson-Kelley mixers, DRAIS turbulence mixers, Lödige mixers, Ruberg mixers, screw mixers, pan mixers, and fluid-bed mixers, as well as continuously operated mixers wherein the polymer particles are mixed as a powder at a rapid frequency using rotating blades (Schugi mixer). Once the secondary crosslinking agent, preferably in the form of a solution, has been mixed with the polymer particles, this is heated at temperatures of from 80 to 250° C., preferably 135 to 250° C., and more preferably 150 to 200° C. to effect surface crosslinking. The optimum time period depends on the type of secondary crosslinker being used and can easily be determined for each crosslinker in a few tests. The time of secondary crosslinking is limited by that point in time where the desired pattern of properties of the superabsorbent polymer product is destroyed as a result of heat damage. In general, the secondary crosslinking time is less than 30 minutes at a temperature of 180° C.

More advantageously, the process according to the invention can be used for the production of polymer gels conventionally produced according to the belt process, because the process of the invention can be carried out on existing belt polymerization plants simply by additionally equipping the corresponding radiation devices, e.g. infrared radiation devices, without further modification of the existing plant technology. The process according to the invention furnishes significantly lower residual amounts of residual monomers, particularly of acrylamide, compared to well-known procedures with no irradiation.

Advantageously, the polymers produced according to the process of the invention are widely usable. For example, water-swellable polymers can be used in the personal care industry, e.g. hygiene industry, in the production of hygiene articles such as absorbent sanitary articles for infant and adult hygiene in the form of baby diapers, sanitary towels, tampons, incontinence articles, as well as products for wound dressing, in which they are incorporated.

Furthermore, such water-swellable polymers can be used in the packaging industry, e.g. in nonwoven products having the water-swellable polymers incorporated therein, e.g. as a packaging component, particularly in the form of absorbent inserts for fish and meat trays.

Moreover, the water-swellable polymers of the invention are used in the form of granulates in agrarian technology or agriculture and horticulture, particularly as soil conditioners for water and nutrient storage, as artificial soils in plant breeding, and as root-protecting gels. In the cable industry and information technology, such water-swellable polymers are used as liquid-absorbing components or as additives in electric or optical fiber cables.

In water-soluble form, the polymers according to the invention are used as flocculation aids, preferably in the clarification of municipal and industrial waste waters, as drilling fluids in petroleum production, as soil improvers, food additives, thickening agents, dispersing aids, retention aids.

The invention will be illustrated with reference to the examples. These explanations are merely given by way of example and do not limit the general idea of the invention.

EXAMPLES

The following abbreviations will be used hereinafter:
ABAH 2,2'-Azobis(2-amidinopropane)hydrochloride
DIMAPA-Quat: 3-Dimethylaminopropyl(meth)acrylamide, quaternized with methyl chloride
ADAME-Quat: 2-Dimethylammoniumethyl(meth)acrylate, quaternized with methyl chloride
Versenex 80 Commercial product of DOW Chemical Company
I. Production of Copolymers from Sodium Acrylate and Acrylamide with a Weight Percentage of 40 Percent Sodium Acrylate Comparative Example Initially, 360.0 g of a 50 wt.-% aqueous acrylamide solution is placed in a polymerization vessel and mixed with 445.9 g of water and 250 mg of Versenex 80. Following addition of 91.9 g of acrylic acid, this was neutralized with 102.1 of a 50 wt.-% aqueous NaOH solution to pH 6.0, cooled to −5° C. and purged with nitrogen. Following addition of 0.45 g of ABAH, polymerization was initiated using UV light. The reaction temperature raised from −5° C. to $T_{max}$=80° C. within 25 minutes. Thereafter, further reaction was allowed for 25 minutes. The polymer product obtained was mashed with a meat grinder and dried at 100° C. for 90 minutes. The product was subsequently milled to a grain fraction of 90 to 1400 μm.

The product had a viscosity of 210 mPas, measured with a Brookfield viscometer on a 0.5% solution in 10% NaCl solution, where the time for dissolution was one hour.

Examples 1 to 3

Polymerization was effected as in the Comparative Example, but this time, this was exposed to a short-wave IR source with a mean wavelength of 1 to 1.5 mm during the secondary reaction time of 20 to 25 minutes, i.e., after reaching $T_{max}$. Control was effected via the surface temperature. Work-up proceeded in an analogous manner as in the Comparative Example. Similarly, the viscosity was around 210 mPas, measured with a Brookfield viscometer on a 0.5% solution in 10% NaCl solution, where the time for dissolution was one hour.

Figure 1:
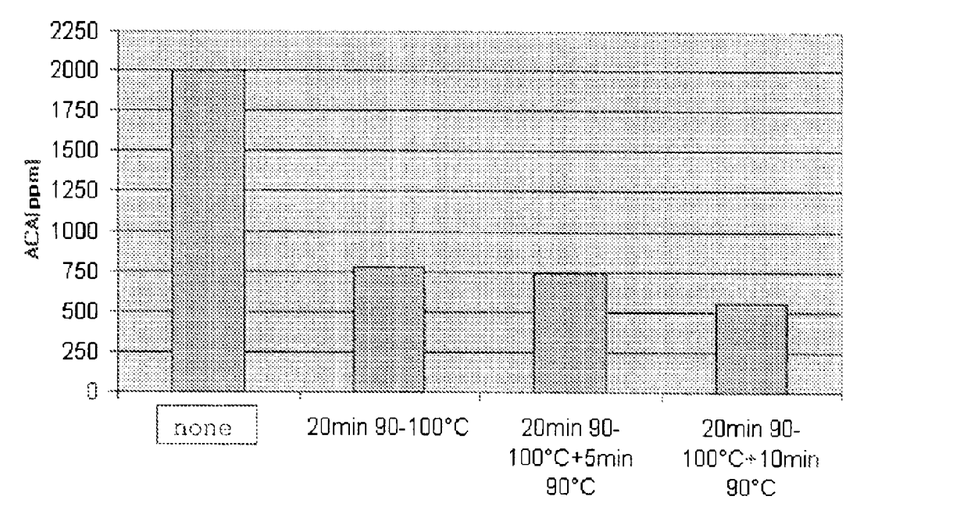
The FIGURE illustrates the detected residual monomer contents from the final products in accordance with the Comparative Example and Examples 1 to 3, respectively.

The Figure illustrates the detected residual monomer contents from the final products in accordance with the Comparative. Example and Examples 1 to 3, respectively.

II. Production of Cationic Copolymers from ADAME-Quat and Acrylamide with 35 Weight Percent ADAME-Quat Examples 4 to 5

Initially, 1040.0 g of a 50% aqueous acrylamide solution was placed in a polymerization vessel and mixed with 1109.0 g of water and 0.75 g of Versenex 80. Following addition of 350.0 g of an 80% ADAME-Quat solution, the pH was adjusted to 5.0 using 0.25 g of 50% sulfuric acid, and this was cooled to 0° C. and purged with nitrogen. Following addition of 1.25 g of ABAH (2,2'-azobis(2-methylpropionamidine) dihydrochloride), polymerization was initiated using UV light. The reaction temperature raised from −5° C. to 80° C. within 25 minutes. At $T_{max}$, the gel was irradiated with an IR source for 10 min (mean wavelength 1 to 1.5 mm). The polymer obtained was mashed with a meat grinder and dried at 100° C. for 90 minutes. The product was subsequently milled to a grain fraction of 90 to 1400 μm. The viscosity was 705 mPas, measured as a 1.0% solution in 10% NaCl solution.

A corresponding comparative batch was run with no irradiation.

The polymer obtained was likewise mashed with a meat grinder, dried at 100° C. for 90 minutes, and the product was milled to a grain fraction of 90 to 1400 μm. The viscosity was 680 mPas, measured as a 1.0% solution in 10% NaCl solution.

In Example 4 according to the invention, the residual monomers were around 640 ppm, and in Comparative Example 5 around 1500 ppm.

The invention claimed is:

1. A process for producing a polymer, comprising polymerizing one or more monomers in solution (monomer solution), said monomer solution containing a photoinitiator or a redox initiator or both to initiate the polymerization, wherein said monomer solution experiences a temperature maximum during polymerization, treating said monomer solution with electromagnetic radiation no earlier than after reaching the maximum temperature of polymerization,
wherein when ultraviolet (UV) radiation is applied to initiate polymerization of the monomer solution and reach a temperature maximum during polymerization, electromagnetic radiation having a wavelength longer than a UV wavelength is employed after reaching the temperature maximum, and subsequently crushing and drying the gel obtained, and
wherein when the photoinitiator is present in the monomer solution, it acts to initiate the polymerization.

2. The process according to claim 1, wherein the monomer solution is polymerized to a monomer conversion of 95 percent before treating with electromagnetic radiation.

3. The process according to claim 1, wherein the monomer solution is polymerized to a monomer conversion of 99 percent before treating with electromagnetic radiation.

4. The process according to claim 1, wherein the electromagnetic radiation is in a frequency range $v=10^9$ to $10^{16}$ Hz, corresponding to a wavelength range $\lambda=35$ cm to 3 nm.

5. The process according to claim 4, wherein the electromagnetic radiation is UV radiation in a wavelength range $\lambda=172$ to 380 nm, corresponding to a frequency range $v=900$ MHz to 140 GHz.

6. The process according to claim 4, wherein the electromagnetic radiation is visible light (VIS radiation) in a wavelength range $\lambda=380$ to 750 nm.

7. The process according to claim 4, wherein the electromagnetic radiation is IR radiation in a wavelength range $\lambda=750$ to 25,000 nm.

8. The process according to claim 1, wherein the monomer solution comprises anionic, non-ionic, cationic and/or amphiphilic ethylenically unsaturated monomers.

9. The process according to claim 8, wherein the monomer solution comprises at least one monomer selected from the group consisting of:

a) olefinically unsaturated carboxylic acids and carboxylic anhydrides, and water-soluble alkali, alkaline earth metal and ammonium salts thereof;
b) olefinically unsaturated sulfonic acids, and water-soluble alkali, alkaline earth metal and ammonium salts thereof;
c) olefinically unsaturated phosphonic acids, and water-soluble alkali, alkaline earth metal and ammonium salts thereof;
d) sulfomethylated and/or phosphonomethylated acrylamides and water-soluble alkali, alkaline earth metal and ammonium salts thereof.

10. The process according to claim 9, wherein:
a) olefinically unsaturated carboxylic acids and carboxylic anhydrides are selected from the group consisting of acrylic acid, methacrylic acid, itaconic acid, crotonic acid, glutaconic acid, maleic acid, maleic anhydride, fumaric acid, and water-soluble alkali, alkaline earth metal and ammonium salts thereof;
b) olefinically unsaturated sulfonic acids are selected from the group consisting of sulfoethyl acrylate, sulfoethyl methacrylate, sulfopropyl acrylate, sulfopropyl methacrylate, 2-hydroxy-3-methacryloxypropylsulfonic acid and 2-acrylamido-2-methylpropanesulfonic acid, and water-soluble alkali, alkaline earth metal and ammonium salts thereof;
c) olefinically unsaturated phosphonic acids are selected from the group consisting of vinyl-and allylphosphonic acid and water-soluble alkali, alkaline earth metal and ammonium salts thereof.

11. The process according to claim 8, wherein the monomer solution comprises at least one non-ionic monomer of general formula (I)

$$CH_2=\underset{R^1}{\overset{}{C}}-\underset{}{\overset{O}{\underset{\|}{C}}}-N\underset{R^3}{\overset{R^2}{\diagdown}} \quad (I)$$

wherein
$R^1$ represents hydrogen or a methyl residue, and
$R^2$ and $R^3$ independently represent hydrogen, an alkyl or hydroxyalkyl residue with 1 to 5 C atoms.

12. The process according to claim 8, wherein the monomer solution comprises at least one monomer of general formula (II)

$$CH_2=\underset{R_1}{\overset{}{C}}-\underset{}{\overset{O}{\underset{\|}{C}}}-Z_1-Y$$

wherein
$R_1$ represents hydrogen or a methyl residue,
$Z_1$ represents O, NH or $NR_4$, with $R_4$ representing an alkyl residue with 1 to 4 C atoms, Y represents one of the groups $$-Y_0-N\underset{Y_3}{\overset{Y_2}{\diagdown}} \quad \text{or} \quad -Y_1-\overset{Y_5}{\underset{Y_7}{N^+}}-Y_6 \quad Z^-$$

wherein
$Y_0$ and $Y_1$ represent an alkylene residue or hydroxyalkylene residue with 2 to 6 C atoms,
each $Y_2$, $Y_3$, $Y_5$, $Y_6$, and $Y_7$ independently represents an alkyl residue with 1 to 6 C atoms,
$Z^-$ represents halogen, acetate, or $SO_4CH_3^-$.

13. The process according to claim 8, wherein the monomer solution comprises at least one amphiphilic monomer of general formula (III) or (IV)

$$CH_2=\underset{R_1}{\overset{}{C}}-\underset{}{\overset{O}{\underset{\|}{C}}}-Z_1-R_4-\overset{R_5}{\underset{R_7}{N^+}}-R_6 \quad Z^- \quad (III)$$

wherein
$Z_1$ represents O, NH, $NR_4$, with $R_4$ representing alkyl with 1 to 4 carbon atoms,
$R_1$ represents hydrogen or a methyl residue,
$R_4$ represents alkylene with 1 to 6 carbon atoms,
$R_5$ and $R_6$ independently represent an alkyl residue with 1 to 6 carbon atoms,
$R_7$ represents an alkyl, aryl and/or aralkyl residue with 8 to 32 carbon atoms, and
Z— represents halogen, pseudohalogen, $SO_4CH_3^-$ or acetate,
or $$CH_2=\underset{R_1}{\overset{}{C}}-\underset{}{\overset{O}{\underset{\|}{C}}}-Z_1-(R_9-O)_n-R_8$$

wherein
$Z_1$ represents O, NH, $NR_4$, with $R_4$ representing alkyl with 1 to 4 carbon atoms,
$R_1$ represents hydrogen or a methyl residue,
$R_8$ represents hydrogen, an alkyl, aryl and/or aralkyl residue with 8 to 32 carbon atoms,
$R_9$ represents an alkylene residue with 2 to 6 carbon atoms, and
n represents an integer of 1 and 50.

14. The process according to claim 1, wherein the composition of the monomer solution comprises 0 to 100 wt.-% of anionic monomers, relative to the overall amount of monomers.

15. The process according to claim 1, wherein the polymerization is carried out on a continuous belt.

16. The process according to claim 1, wherein the polymer is a polyacrylamide.

17. The process according to claim 1, wherein the polymerization is conducted in an adiabatic fashion.

18. The process according to claim 1, wherein when the photoinitiator acts to initiate the polymerization, it is decomposed by the time of treatment with said electromagnetic radiation.

19. The process according to claim 1, wherein the photoinitiator is present in the monomer solution.

20. A process for producing a polymer, comprising polymerizing one or more monomers in solution (monomer solution), wherein said monomer solution experiences a temperature maximum during polymerization, treating said monomer solution with electromagnetic radiation other than radiation optionally applied to initiate the polymerization, no earlier than after reaching the maximum temperature of polymerization, and subsequently crushing and drying the gel obtained, wherein the electromagnetic radiation is visible light (VIS radiation) in a wavelength range $\lambda=380$ to 750 nm or IR radiation in a wavelength range $\lambda=750$ to 25,000 nm.

21. The process according to claim 20, wherein the electromagnetic radiation is said IR radiation.

\* \* \* \* \*